US007084130B2

(12) United States Patent
Shah et al.

(10) Patent No.: US 7,084,130 B2
(45) Date of Patent: Aug. 1, 2006

(54) INTRAOCULAR IRRIGATING SOLUTION HAVING IMPROVED FLOW CHARACTERISTICS

(75) Inventors: Mandar V. Shah, Arlington, TX (US); Mikhail Boukhny, Laguna Niguel, CA (US); William H. Garner, Southlake, TX (US); Kerry L. Markwardt, Mansfield, TX (US); Uday Doshi, Randolph, NJ (US)

(73) Assignee: Alcon, Inc., Hunenberg (CH)

( * ) Notice: Subject to any disclaimer, the term of this patent is extended or adjusted under 35 U.S.C. 154(b) by 407 days.

(21) Appl. No.: 10/240,449

(22) PCT Filed: Dec. 11, 2001

(86) PCT No.: PCT/US01/48094

§ 371 (c)(1),
(2), (4) Date: Sep. 30, 2002

(87) PCT Pub. No.: WO02/49614

PCT Pub. Date: Jun. 27, 2002

(65) Prior Publication Data

US 2003/0109424 A1 Jun. 12, 2003

(51) Int. Cl.
*A61K 31/765* (2006.01)
*A61K 31/717* (2006.01)
*A61K 31/715* (2006.01)

(52) U.S. Cl. .............. 514/54; 514/55; 514/57
(58) Field of Classification Search .......... 514/54, 514/55, 57, 21, 8; 424/78.18
See application file for complete search history.

(56) References Cited

U.S. PATENT DOCUMENTS

| 4,238,482 | A |   | 12/1980 | Peyman et al. |   |
|---|---|---|---|---|---|
| 4,255,415 | A |   | 3/1981 | Chrai et al. |   |
| 4,271,143 | A |   | 6/1981 | Schoenwald et al. |   |
| 4,861,760 | A |   | 8/1989 | Mazuel et al. |   |
| 4,983,585 | A |   | 1/1991 | Pennell et al. |   |
| 5,068,225 | A |   | 11/1991 | Pennell et al. |   |
| 5,328,701 | A |   | 7/1994 | Richmond et al. |   |
| 5,409,904 | A |   | 4/1995 | Hecht et al. |   |
| 5,578,578 | A |   | 11/1996 | Hecht et al. |   |
| 5,895,645 | A | * | 4/1999 | Dabrowski et al. | ...... 424/78.04 |
| 6,174,524 | B1 |   | 1/2001 | Bawa et al. |   |
| 6,271,216 | B1 |   | 8/2001 | Mello et al. |   |
| 6,403,609 | B1 |   | 6/2002 | Asgharian |   |

FOREIGN PATENT DOCUMENTS

| EP | 0 517 970 | 12/1998 |
| EP | 0 938 903 | 9/1999 |
| GB | 2 204 238 | 11/1988 |
| WO | WO 94/10976 | 5/1994 |
| WO | WO 95/07085 | 3/1995 |
| WO | WO 99/51273 | 10/1999 |

OTHER PUBLICATIONS

Assia et al, Journal of Cataract and Refractive Surgery, 1998, 24(1), 78–83.*
Assia, et al. "Experimental Studies on Viscofluids for Intraocular Surgery", *Journal of Cataract and Refractive Surgery*, vol. 24, Jan. 1998, pp. 78–83.
Beesley, et al. "The Effects of Prolonged Phacoemulsification Time on the Corneal Endothelium", *Ann Ophthalmol*, vol. 18, 1986, pp. 216–222.
METHOCEL Cellulose Ethers Technical Handbook, *Dow Chemical Company*, 1997, pp. 1–29.
Edelhauser, et al., "An Intraocular Irrigation Solution Containing AL–8417: In Vitro Evaluation of Effects on Corneal Endothelial Structure and Function", *Investigative Ophthalmology & Visual Science*, Mar. 15, 1998, vol. 39, No. 4, p. S794.
Fernandez–Vigo, et al., "Elimination of Hydroxypropyl Methylcellulose from the Anterior Chamber of the Rabbit", *Journal of Cataract and Refractive Surgery*, vol. 15, Mar. 1989, pp. 191–195.
Fernandez–Vigo, et al., "Molecular Weight Dependence of the Pharmacokinetic of Hydroxypropyl Methylcellulose in the Vitreous", *Journal of Ocular Pharmacology*, vol. 6, No. 2, 1990, pp. 137–142.
"Final Report on the Safety Assessment of Hydroxyethylcellulose, Hydroxypropylcellulose, Methylcellulose, Hydroxypropyl Methylcellulose, and Cellulose Gum", *Journal of the American College of Toxicology*, vol. 5, No. 3, 1986, pp. 1–59.
Gorzinski, et al., "The Fate of Ultra–Low Viscosity $^{14}$C–Hydroxypropyl Methylcellulose in Rats Following Gavage Administration", *Drug and Chemical Toxicology*, vol. 9, No. 2, 1986, pp. 83–100.
Kim, et al., "Scanning Electron Microscopy of the Endothelial Lesion Produced by Air Bubbles During Phacoemulsification With Various Viscoelastics in Human", *Investigative Ophthalmology & Visual Science*, vol. 37, Feb. 15, 1996, No. 3, p. S84.
Kim, et al., "Corneal Endothelial Damage by Air Bubbles During Phacoemulsification", *Archives of Ophthalmology*, vol. 115, Jan. 1997, pp. 81–88.
Kondoh, et al., "Quantitative Measurement of the Volume of Air Bubbles Formed During Ultrasonic Vibration", *Folia Ophthalmol, Japan*, Abstract only. No English Translation.
BSS Plus Overview, *BSS Plus Sterile Intraocular Irrigating Solution*, Alcon intranet information.

(Continued)

*Primary Examiner*—James Wilson
*Assistant Examiner*—Ganapathy Krishnan
(74) *Attorney, Agent, or Firm*—Gregg C. Brown

(57) ABSTRACT

Improved intraocular irrigating solutions are described. The solutions have enhanced viscosities that reduce the risk of damage to intraocular surgical procedures by reducing the turbulence of the solutions and dampening the movement of tissue fragments and air bubbles. The solutions preferably also have modified surface tensions that more closely resemble the surface tension of the aqueous humor.

17 Claims, 2 Drawing Sheets

OTHER PUBLICATIONS

BSS Plus Serile Irrigating Solution (balanced salt solution), *Physicians' Desk Reference for Ophthalmology*, 26th Edition, 1998, p. 209.

Cellugel® Ophthalmic Viscosurgical Device Package Insert, 4 pages.

Celoftal™ Ophthalmic Viscosurgical Device (2% Hydroxypropyl Methylcellulose) Package Insert, 2 pages.

Ocucoat® Viscoadherent (2% Hydroxypropylmethylcellulose) Package Insert, 6 pages.

* cited by examiner

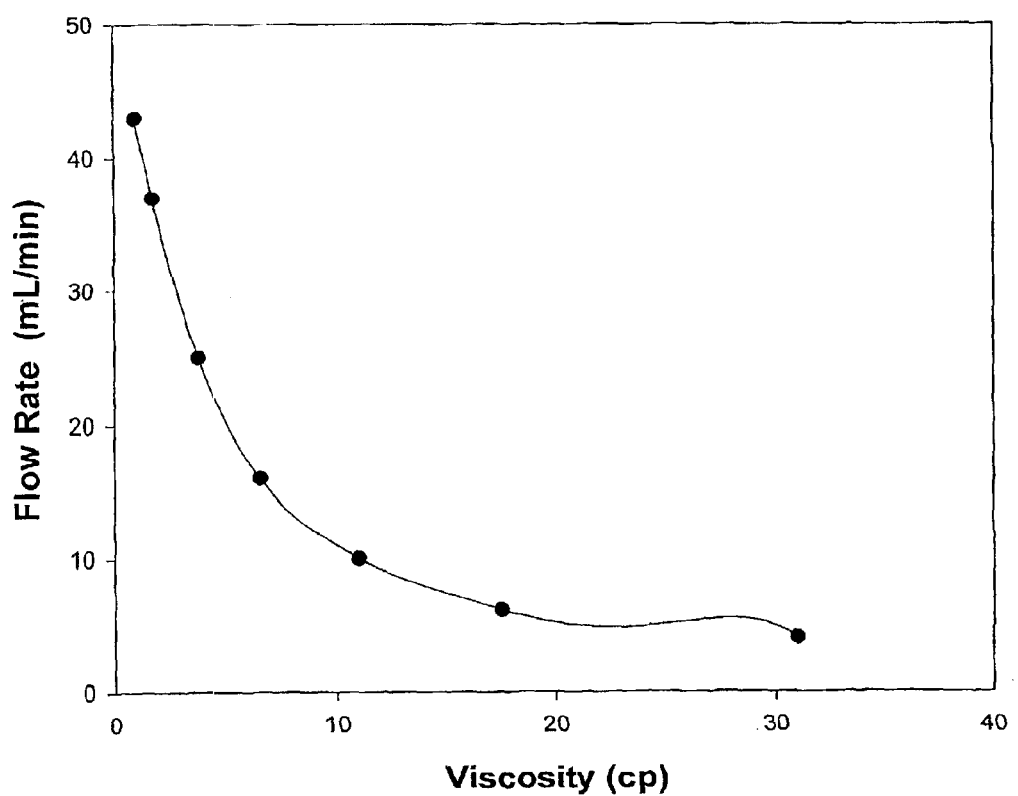
Figure 1. Flow rate of different viscosity irrigating solutions through an irrigation/aspiration tip, using Legacy 20000 at its default settings.

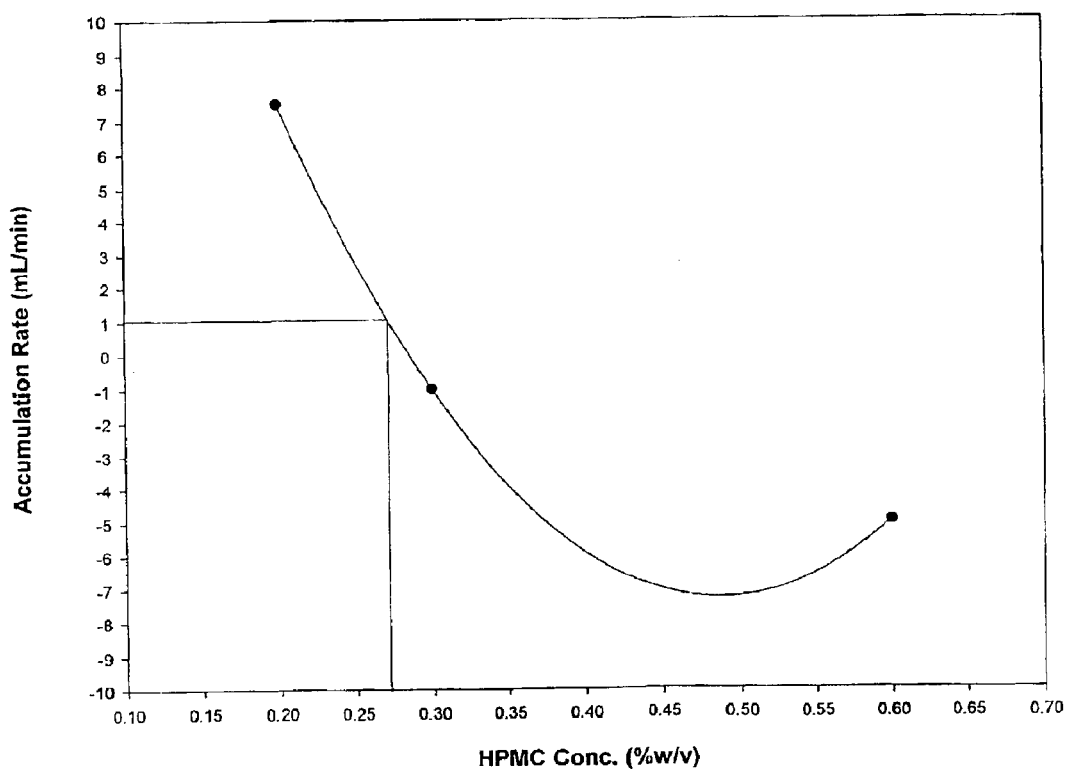
Figure 2. Irrigating solution accumulation at the default settings of Legacy 20000 and at maximum possible vacuum.

INTRAOCULAR IRRIGATING SOLUTION HAVING IMPROVED FLOW CHARACTERISTICS

The present application is a 371 of international Patent Application Number PCT/US01/48094 filed Dec. 11, 2001, which claims benefit of U.S. Provisional Application Ser. No. 60/257,570, filed Dec. 20, 2000.

BACKGROUND OF THE INVENTION

The present invention is directed to the field of intraocular surgery. More specifically, the invention is directed to the irrigation of intraocular tissues during cataract surgery, vitrectomy surgery, and other intraocular surgical procedures. The invention provides intraocular irrigating solutions that have improved physical properties (e.g., flow characteristics) relative to prior ophthalmic irrigating solutions.

The field of intraocular surgery has advanced dramatically over the past twenty years. The advancements in this art have resulted from significant improvements in the areas of surgical techniques, surgical equipment and associated pharmaceutical products. Despite these advancements, intraocular surgery is still a very delicate process with little room for error and great potential for harm to both ocular tissues and, ultimately, the vision of the patient. Thus, there is an ongoing need to improve ophthalmic surgical techniques and equipment, as well as associated pharmaceutical products.

The present invention has resulted from an effort to improve the fluid dynamics of intraocular irrigating solutions, so as to provide greater protection for delicate intraocular tissues, while at the same time enhancing the ability of ophthalmic surgeons to perform surgical procedures more efficiently.

Although various techniques have been used previously to remove the natural crystalline lens of the eye when it becomes afflicted with a cataract, the majority of cataract surgeries today are performed by using a procedure known as "phacoemulsification". This procedure involves the use of a surgical handpiece having a tip that vibrates at an ultrasonic frequency. The vibrating tip of the handpiece is utilized to disintegrate or "emulsify" the cataractous lens. This process necessarily generates lens fragments or particles within the eye that can cause irreparable physical damage to corneal endothelial cells if those cells are left unprotected. The corneal endothelial cells are normally protected during the phacoemulsification procedure by injecting a viscoelastic material (e.g., hyaluronic acid) into the eye to form a protective barrier over the corneal endothelial cells. However, even with the presence of the viscoelastic material, lens particles continue to move in the eye, particularly when the viscoelastic material is removed by a combined irrigating/aspiration handpiece following the phacoemulsification of the lens, prior to insertion of an artificial lens.

Due to continuous irrigation and aspiration, usually there is a lot of turbulence in the anterior chamber, within which non-aspirated lens fragments move around. In addition, the ultrasonic vibrations produced by the tip of the phacoemulsification handpiece push the lens fragments away from the tip thereby making it difficult to aspirate the fragments via the aspiration line in the tip of the handpiece. The movement of these lens fragments can cause damage to the surrounding tissue.

In addition to the lens fragments, damage may result directly from the turbulent flow of fluids intraocularly or from bubbles generated in the intraocular fluids by the phacoemulsification handpiece. Air bubbles generated during intraocular surgery have been shown to result in severe injury to the corneal endothelium in as little as twenty seconds. The turbulent flow of fluids may also cause tissue fragments to impact the delicate corneal endothelial cells or other intraocular tissues, thereby causing mechanical trauma to such tissues.

For further background regarding these problems, please refer to the following articles: Kim, et al., "Corneal endothelial damage by air bubbles during phacoemulsification", *Archives of Ophthalmology*, volume 115, pages 81–88, 1997; Beesley et al., "The effects of prolonged phacoemulsification time on the corneal endothelium", *Annals of Ophthalmology*, volume 18, no. 6, pages 216–219, 1986; Kondoh et al., "Quantitative measurement of the volume of air bubbles formed during ultrasonic vibration", *Folia Ophthalmogica Japan*, volume 45, no. 7, pages 718–720, 1994 and Kim et al., *Investigative Ophthalmology & Visual Science*, volume 37, no. 3, S84, 1996.

The fluid dynamics of intraocular irrigating solutions is also important during vitrectomy procedures and various other types of intraocular surgical procedures. Turbulence in intraocular fluids may also result from the movements of reciprocating vitrectomy handpieces, the alternating vacuum and irrigation modes of irrigation/aspiration handpieces and movements of other surgical handpieces and devices utilized in such procedures. The elimination or reduction of such turbulence helps to protect the retina and other tissues located in the posterior segment of the eye, as well as tissues located in the anterior segment of the eye, such as the corneal endothelial cells.

In view of these potential complications, there is a need for intraocular irrigating solutions having improved physical properties that: (1) reduce the potential for turbulence within the anterior and posterior chambers of the eye, (2) help to contain the movement of tissue fragments and air bubbles within the eye, and (3) facilitate the removal of lens fragments and other tissue fragments by making it easier for the surgeon to track the fragments with the tip of the surgical handpiece. The present invention is directed to fulfilling this need. Specifically, the present invention is directed to the provision of an irrigating solution that provides for greater control of the movement of tissue fragments, air bubbles and other particles during phacoemulsification, vitrectomy and other intraocular surgical procedures. This control of particle movement is fundamentally different from the above-discussed use of a layer of viscoelastic material to protect the corneal endothelial cells by means of a cushioning effect. The irrigating solution of the present invention is designed to provide a protective effect beyond that obtained by means of viscoelastic agents.

SUMMARY OF THE INVENTION

The present invention is directed to the provision of intraocular irrigating solutions that help to prevent the risk of damage to intraocular tissues, while facilitating the efficiency of the surgical procedures. The irrigating solutions of the present invention are low viscosity solutions that exhibit less turbulence in the presence of phacoemulsification handpieces and other intraocular surgical devices. These solutions also restrain the movement of air bubbles and tissue fragments within the eye, and generally dampen the impact of ultrasonic handpieces, liquefracture handpieces, irrigation/aspiration handpieces, microscissors, vitrectomy handpieces and other surgical devices on intraocular tissues.

The restrained movement of lens fragments within the eye protects ophthalmic tissues, and facilitates a more efficient surgical procedure by enabling the ophthalmic surgeon to locate and remove lens fragments more readily.

The intraocular irrigating solutions of the present invention have a viscosity greater than that of aqueous humor, but preferably have a surface tension similar to that of aqueous humor. Existing irrigating solutions generally have a viscosity similar to that of aqueous humor, but have surface tension higher than that of aqueous humor.

The present inventors have found that a slight enhancement of the viscosity of intraocular irrigating solutions greatly improves the ability of the solutions to protect intraocular tissues by containing the movement of tissue fragments and generally reducing the turbulence of the intraocular fluids, thereby making it easier for the fragments to be tracked and removed via aspiration. This slight enhancement of irrigating solution viscosity is also beneficial in vitrectomy procedures because it reduces the pulsatile movement of the retinal tissue and limits collateral tissue damage in the eye. The reduction of pulsatile movement of retinal tissue is particularly important in cases where the retina is partially detached.

The overall performance of the irrigating solutions of the present invention can be further enhanced by including an agent which reduces the surface tension to a level comparable to that of aqueous humor, thereby making the solutions more physiological.

BRIEF DESCRIPTION OF DRAWINGS

FIG. 1 is a graph showing the effect of viscosity on flow rate; and

FIG. 2 is a graph showing the relationship between HPMC concentration and accumulation rate.

DETAILED DESCRIPTION OF THE INVENTION

The irrigating solutions of the present invention comprise a balanced electrolyte solution and an amount of a biologically compatible viscosity-adjusting agent sufficient to enhance the viscosity of the electrolyte solution.

The electrolyte solution utilized in the present invention will typically be a balanced salt solution, such as BSS™ (Balanced Salt Solution) Sterile Irrigating Solution manufactured by Alcon Laboratories, Inc., or BSS PLUS™ (Balanced Salt Solution) Sterile Irrigating Solution, also manufactured by Alcon Laboratories, Inc. However, the invention is not limited relative to the types of balanced salt solutions or other electrolyte/nutrient solutions that may be utilized as a building block for the solutions of the present invention.

The agents utilized to adjust the viscosity of the electrolyte solution will comprise one or more compounds that are compatible with intraocular tissues, such as: chondroitin sulfate, sodium hyaluronate or other proteoglycans; cellulose derivatives, such as hydroxypropyl methylcellulose ("HPMC"), carboxy methylcellulose ("CMC"), and hydroxyethyl cellulose ("HEC"); collagen and modified collagens; galactomannans, such as guar gum, locust bean gum and tara gum, as well as polysaccharides derived from the foregoing natural gums and similar natural or synthetic gums containing mannose and/or galactose moieties as the main structural components (e.g., hydroxypropyl guar); xanthan gum; gellan gums; alginate; chitosans; polyvinyl alcohol; carboxyvinyl polymers (e.g., carbomers such as the Carbopol™ brand polymers available from B.F. Goodrich); and various other viscous or viscoelastomeric substances, including but not limited to those described in U.S. Pat. No. 5,409,904 (Hecht, et al.), the entire contents of which are hereby incorporated by reference in the present specification.

The following patent publications may be referred to for further details concerning the above-listed viscosity-enhancing agents: U.S. Pat. No. 4,861,760 (gellan gums); U.S. Pat. No. 4,255,415 and WIPO Publication No. WO 94/10976 (polyvinyl alcohol); U.S. Pat. No. 4,271,143 (carboxyvinyl polymers); WIPO Publication No. WO 99/51273 (xanthan gum); and WIPO Publication No. WO 99/06023 (galactomannans). The entire contents of the foregoing references pertaining to the structures, chemical properties and physical properties of the respective viscosity enhancing agents described above are hereby incorporated in the present specification by reference.

The above-described viscosity-adjusting agents will be utilized in an amount sufficient to provide the irrigating solutions of the present invention with an enhanced viscosity. As utilized herein, the phrase "enhanced viscosity" means a viscosity which is greater than the viscosity of aqueous humor and prior irrigating solutions, both of which generally have viscosities of approximately 1 centipoise ("cps"). The irrigating solutions of the present invention will typically have viscosities of from greater than 1 cps to about 15 cps, preferably from about 2 to about 7 cps.

The amount of viscosity adjusting agent utilized will vary depending on the degree of viscosity enhancement desired and the specific agent or agents selected. However, the concentration of the viscosity-adjusting agent in the irrigating solutions of the present invention will typically range from about 0.1 to about 1.0 weight/volume percent ("w/v %") for polymers such as HPMC.

It should be noted that it is necessary to achieve a balance between: (a) enhancing the viscosity of the solution, and (b) maintaining a solution viscosity that is acceptable for use with the irrigation/aspiration system employed during intraocular surgical procedures. FIG. 1 of the accompanying drawings is a graph showing the flow rate of irrigating solutions of different viscosities through a normal irrigation/aspiration tip in the Series 20000 Legacy™ ("STTL") surgical operating system available from Alcon Laboratories, Inc. During generation of these data, all the settings on the STTL system were default instrumental settings. FIG. 1 clearly shows the effect of increasing viscosity on flow rate of the irrigating solution, which is usually flowing under gravity.

During a surgical procedure, aspiration is carried out by applying vacuum through the tip of a surgical handpiece. Generally, the maximum vacuum or suction capability of the system is such that the irrigation rate is higher than the aspiration rate to maintain positive flow. Hence, the increase in viscosity of the irrigation solution should be such that the flow rate remains greater than the maximum aspiration rate. FIG. 2 of the accompanying drawings illustrates this point.

Increasing the concentration of the viscosity-adjusting agent increases the viscosity of the solution, so at the same bottle height, the normal gravity fed irrigation flow rate of fluid into the eye decreases. As the net irrigation rate decreases, the effective aspiration rate, which is controlled independently by a peristaltic pump on the STTL, increases. Hence, the accumulation rate goes from a positive to a negative value. A minimum irrigation rate of 1 milliliter/minute of aspiration is needed to prevent drying up of the tissue. These competing factors must be balanced. In the case of HPMC, it has been determined that a HPMC concentration of 0.27 w/v % provides the desired level of viscosity enhancement without impeding normal irrigation and aspiration functions. It should be noted that this ideal concentration was determined using HPMC (E4M) in connection with the STTL surgical operating system and a standard phacoemulsification tip. The ideal concentration may vary somewhat, depending on the surgical operating system and phacoemulsification tip utilized.

The preferred viscosity-adjusting agent is hydroxypropylmethylcellulose ("HPMC"). The present inventors have found that the addition of HPMC to a conventional balanced salt solution results in a significant reduction in turbulence during intraocular surgery, relative to the turbulence seen with the balanced salt solution alone. The preferred concentration of HPMC is about 0.2 to 0.3 w/v %, but this range may vary slightly depending on the particular ophthalmic surgical system being utilized and the instrument settings of that system. Irrigating solutions containing this concentration of HPMC will have a viscosity of about 4 to 6 cps. The most preferred viscosity-adjusting agent is HPMC (E4M) at a concentration of 0.22 to 0.27 w/v %.

As indicated above, the irrigating solutions of the present invention preferably also include an agent to modify the surface tension of the solutions so as to resemble the surface tension of the aqueous humor. The surface tension of the aqueous humor is approximately 50 dynes per centimeter ("dynes/cm"). The irrigating solutions of the present invention will therefore preferably have a surface tension in the range of 40 to 60 dynes/cm or somewhat less.

It should be noted here that viscosity can be increased by an appropriate agent without affecting surface tension, and that surface tension can be reduced to the level of aqueous/vitreous humor by inclusion of an appropriate surface-active agent independent of viscosity. Thus, these two physical properties of irrigating solutions are independent of each other. However, in some cases, the viscosity-adjusting agent may also function as the surface tension reducing agent. This is true with respect to the preferred embodiment of the present invention, wherein HPMC is utilized both as a viscosity-adjusting agent and a surface tension reducing agent.

In other cases, it may be necessary to add a separate agent to the irrigating solution for purposes of reducing the surface tension of the solution. Possible agents which can be utilized for this purpose include: Polyoxyl 35 castor oil (Cremophore™ EL and Cremophore™ EL-P, available from BASF Corp.), Polyoxyl 40 Hydrogenated Castor Oil (HCO-40), Solutol™ HS 15 (BASF Corp.), Polysorbate 80, Tocophersolan (TPGS), and other ophthalmically acceptable surface active agents.

The following examples are provided to further illustrate various features of the present invention.

EXAMPLE 1

| Component | Amount (w/v %) | Function |
| --- | --- | --- |
| HPMC (E4M) | 0.1 to 0.3 | Viscosity and Surface Tension Modifier |
| Sodium Chloride | 0.744 | Tonicity Agent |
| Potassium Chloride | 0.0395 | Essential Ion |

-continued

| Component | Amount (w/v %) | Function |
| --- | --- | --- |
| Dibasic Sodium Phosphate (Anhydrous) | 0.0433 | Buffering Agent |
| Sodium Bicarbonate | 0.219% + 20% xs | Physiological Buffer |
| Hydrochloric Acid | Adjust pH | pH Adjust |
| Sodium Hydroxide | Adjust pH | pH Adjust |
| Water for Injection | 100% | Vehicle |

The above-described formulation may be prepared as follows: First, the water for Injection is brought close to boiling or at boiling. The HPMC is then slowly added to the water under continuous stirring to thoroughly disperse it in the water. Then the mixture is slowly allowed to cool, stirring continuously. Once at room temperature, the mixture should start clearing up. Then the mixture is stored overnight in an appropriate container to fully hydrate the HPMC. The following day, the remaining ingredients are added to the HPMC solution, additional water for injection is added if needed to bring the solution to final volume, and the final solution is filtered, packaged in bottles and autoclaved.

EXAMPLE 2

| Component | Amount (w/v %) | Function |
| --- | --- | --- |
| HPMC (E4M) | 0.1 to 0.3 | Viscosity and Surface Tension Modifier |
| Sodium Chloride | 0.64 | Tonicity Agent |
| Potassium Chloride | 0.075 | Essential Ion |
| Calcium Chloride (Dihydrate) | 0.048 | Essential Ion |
| Magnesium Chloride (Hexahydrate) | 0.03 | Essential Ion |
| Sodium Acetate (Trihydrate) | 0.039 | Buffering Agent |
| Sodium Citrate (Dihydrate) | 0.17 | Buffering Agent |
| Hydrochloric Acid | Adjust pH | pH Adjust |
| Sodium Hydroxide | Adjust pH | pH Adjust |
| Water for Injection | 100% | Vehicle |

The above-described formulation may be prepared by means of the method described in Example 1, above.

EXAMPLE 3

Three solutions were prepared and tested to evaluate the physical properties of the solutions of the present invention versus related solutions. The solutions tested and the respective physical properties of the solutions were as follows:

| Solution | Osmolality mOsm/kg | Viscosity (cps) | Surface Tension dynes/cm$^2$ |
| --- | --- | --- | --- |
| BSS* | 304, 305 | 1.02, 1.06 | 70, 73 |
| BSS + 0.05% cremophor | 305, 305 | 0.99, 1.01 | 43, 43 |
| BSS + 0.3% HPMC (grade E4M) | 320, 322 | 6.9, 7.0 | 48, 49 |

*As utilized in the above table, the term "BSS" refers to BSS ™ (Balanced Salt Solution) Sterile Irrigating solution manufactured by Alcon Laboratories, Inc., Fort Worth, Texas.

As indicated above, the addition of 0.3% HPMC to the BSS solution increased the viscosity from approximately 1 cps to 7 cps, and reduced the surface tension from approximately 71.5 dynes/cm to approximately 48.5 dynes/cm. Thus, the addition of this amount of HPMC increased the viscosity of the balanced salt solution and reduced its surface tension, in accordance with the basic principles of the present invention. Conversely, the addition of 0.05% cremophor to the balanced salt solution had no effect on viscosity, but reduced the surface tension of the balanced salt solution from approximately 71.5 dynes/cm to 43 dynes/cm.

The above-identified solutions were tested in a simulated intraocular surgery model to determine if the addition of cremophor and HPMC to the balanced salt solution affected the performance of the solution relative to the turbulence of the solution during intraocular surgical procedures. It was determined that the addition of cremophor to the balanced salt solution, although effective in reducing the surface tension of the solution, had little if any effect on the performance of the balanced salt solution. However, the solution containing HPMC demonstrated much less turbulence than the balanced salt solution alone. This turbulence was judged based on the movement of air bubbles and the movement of lens fragments.

The spinning and rotation of lens fragments seen with the balanced salt solution alone was reduced significantly by the inclusion of HPMC in the solution. The dampening of the movement of the lens particles facilitated an easier removal of the particles from the eye during the simulated surgical procedure. This dampening effect facilitated a more efficient surgical procedure and reduced the time required for the procedure.

Conversely, there appeared to be no difference between the balanced salt solution alone and the balanced salt solution containing cremophor with regard to bubble formulation, rate of flow or the visual hydrodynamics of the irrigating solutions.

The foregoing results confirm that the addition of a small amount of a viscosity enhancing agent reduces the turbulence of intraocular fluids during surgical procedures, dampens the movement of bubbles and lens fragments, and generally renders the procedure more efficient.

We claim:

1. An ophthalmic pharmaceutical composition for irrigating ocular tissues during an intraocular surgical procedure, comprising a balanced salt solution and an amount of a viscosity-adjusting agent sufficient to provide the composition with a viscosity of 2 to 7 cps, said composition having a surface tension of 40 to 60 dynes/cm.

2. A composition according to claim 1, wherein the viscosity-adjusting agent is selected from the group consisting of proteoglycans, cellulose derivatives, collagen or modified collagen, galactomannans, xanthan gums, gellan gums, alginate, chitosans, polyvinyl alcohol, and carboxyvinyl polymers.

3. A composition according to claim 2, wherein the viscosity-adjusting agent comprises a cellulose derivative.

4. A composition according to claim 3, wherein the viscosity-adjusting agent comprises hydroxypropyl methylcellulose.

5. A composition according to claim 4, wherein the concentration of hydroxypropyl methylcellulose in the composition is 0.1 to 1.0 w/v %.

6. A composition according to claim 5, wherein the concentration of hydroxypropyl methylcellulose in the composition is 0.1 to 0.3 w/v %.

7. A composition according to claim 6, wherein the concentration of hydroxypropyl methylcellulose in the composition is 0.2 to 0.3 w/v %.

8. A composition according to any one of claims 1 to 7, wherein the balanced salt solution is an electrolyte/nutrient solution.

9. A method of irrigating intraocular tissues during an ophthalmic surgical procedure, which comprises bathing the intraocular tissues with an irrigating solution containing an amount of a viscosity-adjusting agent sufficient to provide the solution with a viscosity of 2 to 7 cps, whereby the turbulence of the solution during the surgical procedure is reduced.

10. A method according to claim 9, wherein the viscosity-adjusting agent is selected from the group consisting of proteoglycans, cellulose derivatives, collagen or modified collagen, galactomannans, xanthan gums, gellan gums, alginate, chitosans, polyvinyl alcohol, and carboxyvinyl polymers.

11. A method according to claim 10, wherein the viscosity-adjusting agent comprises a cellulose derivative.

12. A method according to claim 11, wherein the viscosity-adjusting agent comprises hydroxypropyl methyl cellulose.

13. A method according to claim 12, wherein the concentration of hydroxypropyl methylcellulose in the solution is 0.1 to 1.0 w/v %.

14. A method according to claim 13, wherein the concentration of hydroxypropyl methylcellulose in the solution is 0.1 to 0.3 w/v %.

15. A method according to claim 14, wherein the concentration of hydroxypropyl methylcellulose in the solution is 0.2 to 0.3 w/v %.

16. A method according to any one of claims 9 to 15, wherein the irrigating solution has a surface tension of 40 to 60 dynes/cm.

17. A method according to any one of claims 9 to 15, wherein the irrigating solution is an electrolyte/nutrient solution.

* * * * *